US005728580A

United States Patent [19]
Shuler et al.

[11] Patent Number: 5,728,580
[45] Date of Patent: Mar. 17, 1998

[54] METHODS AND CULTURE MEDIA FOR INDUCING SINGLE CELL SUSPENSION IN INSECT CELL LINES

[75] Inventors: Michael L. Shuler; Kennie U. Dee, both of Ithaca, N.Y.

[73] Assignee: Cornell Research Foundation, Inc., Ithaca, N.Y.

[21] Appl. No.: 603,722

[22] Filed: Feb. 20, 1996

[51] Int. Cl.$^6$ ................................................ C12N 1/00
[52] U.S. Cl. ........................... 435/348; 435/383; 435/384; 435/405
[58] Field of Search ........................... 435/240.1, 240.21, 435/240.25, 348, 383, 384, 405, 325

[56] References Cited

U.S. PATENT DOCUMENTS

| | | | |
|---|---|---|---|
| 4,786,599 | 11/1988 | Chessebeuf et al. | 435/240.31 |
| 4,879,236 | 11/1989 | Smith et al. | 435/235 |
| 4,994,387 | 2/1991 | Levine et al. | 435/240.2 |
| 5,024,947 | 6/1991 | Inlow et al. | 435/240.31 |
| 5,132,223 | 7/1992 | Levine et al. | 435/240.2 |
| 5,318,898 | 6/1994 | Israel | 435/69.1 |
| 5,348,877 | 9/1994 | McKenna et al. | 435/240.21 |
| 5,501,971 | 3/1996 | Freedman et al. | 435/240.23 |

OTHER PUBLICATIONS

Wu, J. Et al, 1990, "Adaptation of Insect cells to suspension culture", J. Ferment. Bioeng. 70: 90–93.

Ogonah, O., et al, 1991, "Protein production (B–galactosidase) from a baculovirus vector in Spodoptera frugiperada and Trichopulsia ni cells in suspension culture", Biotech. Lett. 13: 265–270.

Hink, W.F., et al, 1976, "Growth of Trichoplusia ni (Tn368) cell line in suspension culture", pp. 297–300 In: E. Kurstak et al (ed), Invertebrate tissue culture, Academic Press, New York.

Chalmers, et al, 1995, "The effect of hydrodynamic forces in insect cells", 175–204. In: M.L. Shuler et al (ed) Baculovirus expression systems and biopesticides, Wiley–Liss, New York.

Taticek, R., 1995, "Enhanced recombinant protein expression in baculovirus–infected high–density insect cell suspension cultures and the operation of a continuous flow bioreactor"., Ph.D. thesis, Cornell Univ. Ithaca, NY.

Overton, L. Et al, "Potential application of insect cell–based expression systems in the bio/pharmaceutical industry", 233–242. In: M.L. Shuler et al, (ed) Baculovirus expression systems and biopesticides, Wiley–Liss, NY.

Wickham, et al. et al, 1993, "Optimization of growth methods and recombinant protein production in BTI–Tn5B1–4 insect cells using the baculovirus expression system", Biotechnol. Prog. 9: 25–30.

Chung, et al et al, 1993, "Production of human alkaline phosphatase, a secreted, glycosylated protein, from a baculovirus expression system and the attachment–dependent cell line Trichoplusia ni BTI–Tn5B1–4 using a split–flow air–lift bioreactor", Biotechnol. Prog. 9:675–678.

Carroll et al, 1982, "Heparin–binding Agglutinin On Human Teratocarcinoma Cells: Biochem. Biophys. Res. Commun.", 109/4, pp. 1353–1359.

Gill et al, 1986, Heparin–Induced Aggregation of Lymphoid Cells, J. Cell. Physiol., 126/3, pp. 352–358.

Moore et al, Heparin–induced Agglutination of Erythrocytes in Horses, Amer. Jnl. Of Veterinary Res., 48 (1).

Mahaffey et al, 1986, Erythrocyte Agglutination Associated With Heparin Treatment In Three Horses, Jn. Amer. Veterinary Medical Assoc., 189 (11): 1478–1480.

Dougherty et al, 1981, Physical Factors That Affect In Vitro Autographica Californica Nuclear Polyhedrosis Virus Infection, Applied and Environmental Microbiology, pp. 1166–1172.

Karlsson et al, 1989, Binding of Human Extracellular–Superoxide Dismutase C. To Cultured Cell Lines and to Blood Cells, Lab. Investigation, 60(5): 659–666.

Oberlander et al, 1987, Abstract, Archives of Insect Biochemistry and Physiology, 5 (2): 81–89.

*Primary Examiner*—David M. Naff
*Assistant Examiner*—Deborah K. Ware
*Attorney, Agent, or Firm*—Brown, Pinnisi & Michaels

[57] ABSTRACT

Non-carboxylated sulfated polyanions have been successfully used to rapidly obtain and maintain stable single-cell suspension of BTI-TN5B1-4 cells, a cell line which has a high intrinsic capacity for the expression of recombinant protein, but which clumps severely in suspension reducing its effectiveness as a host for foreign protein production with the baculovirus expression vector system. The three most effective polyanions for inducing a single-cell suspension were dextran sulfate, polyvinyl sulfate, and pentosan sulfate. The cost of dextran sulfate treatment is low compared to heparin treatment, which required a 20-fold higher lever to induce single-cell suspension. More importantly, dextran sulfate does not block vital infection at MOI≧1 whereas heparin is known to seriously inhibit infection. To overcome this effect, the cells can be subcultured to a fresh culture medium without the sulfated polyanion, or the sulfated polyanion is neutralized with a polycation, then the cells are inoculated with the baculovirus. Once the cells are infected with the baculovirus, the sulfate polyanion is added back to the fresh culture medium. Inducing single-cell suspension with dextran sulfate, a highly sulfated polyanion, resulted in an increased volumetric yield of recombinant protein. Examples chosen for experimentation included, human secreted alkaline phosphatase, and b-galactosidase. Optimum volumetric yield of 6 to 11 fold higher than attached cells for the production of alkaline phosphatase in BTI-TN5B1-4 dextran sulfate cells under elevated oxygen. More importantly, cells can be infected at high density without complications from aggregation, which has important implications for scale-up.

12 Claims, 2 Drawing Sheets

METHODS AND CULTURE MEDIA FOR INDUCING SINGLE CELL SUSPENSION IN INSECT CELL LINES

ACKNOWLEDGMENT OF GOVERNMENT SUPPORT

This invention was made with Government support under Grant No. BES-9412249, awarded by the National Science Foundation. The government has certain rights in the invention.

FIELD OF THE INVENTION

The invention pertains to the field of propagation of cell lines. More particularly, the invention pertains to methods of propagating cells in suspension.

BACKGROUND OF THE INVENTION

The past decade has witnessed the rapid emergence of genetic engineering technology coupled with major improvements in the development of large-scale insect cell culture processes. These developments have led to the widespread use of insect cells as a valuable host cell system for the expression of recombinant proteins.

The insect cell-baculovirus expression system has been used extensively to produce recombinant proteins. A significant advantage of this system is the high expression levels, up to 250-fold greater than in mammalian expression systems, which can be achieved very rapidly. In addition, insect cells perform most of the post-translational modifications of mammalian cells, including glycosylation, and most of the proteins expressed retain biological function.

High levels of some recombinant proteins have been achieved, approaching the levels of the native polyhedrin protein from the baculovirus (1000 mg/L). However, expression of glycosylated, secreted proteins in the commonly used Spodoptera frugiperda cell lines SF9 and SF21 is much lower. SF9 is a clonal isolate of SF21 but in general produces about the same levels of recombinant proteins. Many secreted glycosylated proteins are produced in SF9 cells at levels below 10 mg/L.

One of the insect cell lines which has shown great promise is BTI-Tn-5B1-4, hereafter referred to as TN5B1-4, established at Boyce Thompson Institute, Ithaca, N.Y. and commercially available for use in research as High Five™ cells from Invitrogen Corp. The cell line is on deposit at the American Type Culture Collection as ATCC CRL 10859. This novel cell line is the subject of U.S. Pat. No. 5,300,435, filed Dec. 1, 1992. These cells were derived from eggs of the Cabbage Looper (Trichoplusia ni) and have been found to be particularly susceptible to baculoviruses, which are adaptable to genetic modifications which lead to high levels of secretion of proteins and have been shown to be superior to SF9 for expression of both cytoplasmic and secreted glycosylated proteins. TN5B1-4 optimally produced 7-fold more b-galactosidase, 26-fold more human secreted alkaline phosphatase (SEAP), and 28-fold more soluble tissue factor per cell than SF9 in monolayer cultures. However, TN5B1-4 clumps severely in suspension while SF9 does not. SF9 can be readily grown in suspension and infected at high cell density without significantly affecting their per cell production.

Cell lines derived from Trichoplusia ni are difficult to grow in suspension. Wu et al. reported poor cell growth for TN368 cells in shake flasks. (Wu, J., King, G., Daugulis, A. J., Faulkner, P., Bone, D. H., Goosen, M. F. A. 1990. Adaptation of insect cells to suspension culture. J. Ferment. Bioeng. 70: 90–93.) Ogonah et al. found that TN368 cells grown in spinner flasks can be maintained for only 30–50 days and protein production was erratic. (Ogonah, O., Shuler, M. L., Granados, R. R. 1991. Protein production (β-galactosidase) from a baculovirus vector in Spodoptera frugiperda and Trichoplusia ni cells in suspension culture. Biotech. Lett. 13: 265–270.) Hink and Strauss alleviated clumping of TN368 (another Trichoplusia ni cell line) cells by adding methylcellulose, but could not eliminate clumping completely. (Hink, W. F., Strauss, E. M. 1976. Growth of Trichoplusia ni (Tn368) cell line in suspension culture, pp. 297–300. In: E. Kurstak and K. Maramorosch (ed.), Invertebrate tissue culture, Academic Press, New York.) Chalmers et al. reported that cell damage occurs at the shear stress required to induce single-cell formation of TN368 cells. (Chalmers, J. J. 1995. The effect of hydrodynamic forces on insect cells, 175–204. In: M. L. Shuler, H. A. Wood, R. R. Granados and D. A. Hammer (ed), Baculovirus expression systems and biopesticides, Wiley-Liss, New York.) Taticek selected for single cells from suspension culture of TN5B1-4 but these cells eventually aggregated severely. (Taticek, R. 1995. Enhanced recombinant protein expression in baculovirus-infected high-density insect cell suspension cultures and the operation of a continuous flow bioreactor. Ph.D. thesis, Cornell University, Ithaca, N.Y.) Taticek also used higher agitation speed in spinner flasks (ca. 160 rpm) which reduced aggregation but could not maintain good cell growth after 20–30 passages.

Reports on attempts to scale-up protein production in TN5B1-4 cells are limited, because of the problems associated with growing these cells in suspension. Overton and Kost used suspension culture of TN5B1-4 in a 5-L airlift fermentor to produce the secreted protein tissue inhibitor of metalloproteinases, but the volumetric yield was not significantly higher than adherent cultures. (Overton, L. K., Kost, T. A. 1995. Potential application of insect cell-based expression systems in the bio/pharmaceutical industry, 233–242. In: M. L. Shuler, H. A. Wood, R. R. Granados and D. A. Hammer (ed), Baculovirus expression systems and biopesticides, Wiley-Liss, New York.) Wickham and Nemerow used roller bottles coated with DEAE-based microcarriers to scale-up attached cultures to 5 L and obtained yields of 5–26 mg/L of soluble tissue factor. (Wickham, T. J., Nemerow, G. R. 1993. Optimization of growth methods and recombinant protein production in BTI-Tn5B1-4 insect cells using the baculovirus expression system. Biotechnol. Prog. 9: 25–30.) Chung et al. proposed using a split-flow, air-lift reactor with cells attached to glass beads in the downcomer section, and reported a volumetric yield of 10.7 mg/L of secreted alkaline phosphatase for a 0.5-L unit. (Chung, I. S., Taticek, R. A., Shuler, M. L. 1993. Production of human alkaline phosphatase, a secreted, glycosylated protein, from a baculovirus expression system and the attachment-dependent cell line Trichoplusia ni BTI-Tn5B1-4 using a split-flow air-lift bioreactor. Biotechnol. Prog. 9: 675–678.) Other scale-up strategies in attached cultures have been less successful. For example, TN5B1-4 cells do not grow well in roller bottles, and induce clumping of DEAE-based microcarrier beads by cell-cell bridging.

Protein production of cell lines derived from Trichoplusia ni in monolayer culture is severely inhibited by cell—cell contact which has been suggested to induce synthesis of an intracellular inhibitory metabolite. Thus, for optimum per cell production, TN5B1-4 cells are usually infected at low surface coverage of 10–20 percent. Protein production using TN5B1-4 cells in attached cultures is therefore not efficient.

SF9 and SF21 cells can be readily infected in suspension at high cell density to obtain volumetric yields equal to or greater than attached cultures of TN5B1-4 cells.

Aggregate culture of TN5B1-4 in suspension may be poor producers due to contact-like inhibition, due to diffusional barriers for nutrients or metabolic by-products, or due to reduced accessibility to virus. The per cell production of recombinant proteins in TN5B1-4 cells drops drastically for infection at cell densities higher than $1\times10^6$ cells/ml in spinner flasks with commercial media and with an air atmosphere. Elimination of contact inhibition by inducing formation of single cells may be the key to exploiting the intrinsic advantages of TN5B1-4 over SF9 and SF21 cells.

Because of the shear sensitivity of *T. ni* cells, increasing the shear rate is not a practical approach for inducing single-cell formation. A more rational solution would be to find a dispersing agent, such as a substrate that competitively binds to the adhesion receptor(s) and thus block aggregation. There is, however, no known additive with an intrinsic capacity to induce single-cell formation, and isolating the adhesion receptor would be tedious and difficult.

The use of heparin, a sulfated and carboxylated polysaccharide, has been reported to eliminate clumping in suspension culture of TN5B1-4 cells and was the subject of U.S. Pat. No. 5,348,877. However, heparin is expensive and inhibits viral infection resulting in poor protein production due to significant cell growth during infection which competes for nutrients. Since heparin had already been shown to induce single cell formation in TN5B1-4 cells, an effort was made to determine what structural features of heparin are important, which would hopefully lead to the identification of more effective dispersing agents that are potentially less inhibitory to viral infection.

The present inventors have successfully identified low-cost compounds that effectively eliminate clumping of insect cells in suspension culture. Specifically, the inventors have discovered that dextran sulfate and other sulfated polyanions can be used to increase protein production in the insect cell baculovirus system where a viral vector is involved.

U.S. Pat. No. 5,318,898 discloses the use of dextran sulfate to increase recombinant protein in transformed mammalian host cells. This patent covers mammalian host cells transformed with a DNA encoding the recombinant protein but does not include recombinant protein production in expression systems where virus vectors carrying the recombinant genes are used, as in the case of the insect-cell baculovirus system.

There is extensive relevant art for the use of sulfated polyanions to block viral infection. Similar inhibition of viral infection has been disclosed in the insect-cell baculovirus system at high levels of polyanions. It is therefore unexpected that dextran sulfate or sulfated polyanions in general can be used to increase protein production in the insect cell-baculovirus system where a viral vector is involved; inhibition of viral infection will naturally lead to inhibition of protein production.

Pat. Nos. 5,132,223 and 4,994,387 disclosing a medium containing dextran sulfate to replace heparin for the cultivation of human endothelial cells. In these patents, dextran sulfate was used to enhance cell growth and prolong the lifespan of endothelial cells. These patents are not relevant to the use of dextran sulfate or sulfated polyanions for inducing single cell suspension of insect cells. In particular, endothelials cells are obligate anchorage-dependent cells, ie., they grow only when attached to surfaces. In fact, because endothelial cells do not grow in suspension, the word "suspension" was not used in these patents.

U.S. Pat. No. 4,786,599 discloses a serum-free animal cell medium and method, for the primary culture and production of cell lines using the medium. The patent discloses the use of lipophilic biopolymers such as dextran for the dissolution of fatty acids. Dextran and Pluronic F68, two polymers commonly used to dissolve fatty acids, do not induce single-cell suspension of Tn5B1-4 cells. This patent does not disclose the use of sulfated polyanions to induce single-cell suspension or enhancement of protein production.

U.S. Pat. No. 4,786,599 discloses a serum-free animal cell medium and method, for the primary culture and production of cell lines using the medium. The patent discloses the use of lipophilic biopolymers such as dextran for the dissolution of fatty acids. Dextran and Pluronic F68, two polymers commonly used to dissolve fatty acids, do not induce single-cell suspension of Tn5B1-4 cells. This patent does not disclose the use of sulfated polyanions to induce single-cell suspension or enhancement of protein production.

U.S. Pat. No. 5,024,947 discloses a serum-free media including a protective agent, such as dextran sulfate for the growth of insect cells and expression of products thereof. In this patent, protective agents are defined as "non-toxic, water soluble compounds that functionally act to protect insect cells from damage and death in agitated and sparged insect cell culture". In other words, protective agents are shear protectants. This patent does not teach that sulfated polyanions can induce single-cell suspension and enhance recombinant protein production. First, the two widely used protective agents, sodium CMC and Pluronic F68, do not induce single-cell suspension. Second, concentrations of 0.1% or greater are required for shear protection. In the case of dextran sulfate, the concentrations required for inducing single-cell suspension are not high enough to potentially exhibit any shear protection. At concentrations required for shear protection, dextran sulfate will be inhibitory to viral infection, i.e. protein production will be inhibited. In addition, our work indicates that dextran sulfate is toxic at concentrations greater than 0.1% so that it may become toxic before any shear protection is possible.

U.S. Pat. No. 5,348,877 teaches a method of adapting anchorage-dependent insect cell lines to suspension conditions using heparin. Heparin is not very effective in inducing single-cell suspension. A 20 fold higher heparin concentration is required relative to dextran sulfate. At concentrations required to induce single cell suspension, heparin inhibits viral infection resulting in poorer yield of recombinant protein compared to clumped cultures. This patent does not teach that a concomitant increase in protein yield is possible from inducing single-cell suspension. More importantly, this patent does not cover other sulfated polyanions such as dextran sulfate that can be used at much lower levels without inhibiting viral infection.

The use of non-carboxylated sulfated polyanions to induce single cell suspension in the insect cells is not described elsewhere in the literature. In mammalian cells, the results are not clear-cut. For example, heparin induces aggregation of lymphoid cells (Thurn and Underhill, 1986), and polyanions such a dextran sulfate induce aggregation of lymphocyte cells (Nakashima et al, 1993). On the other hand, high MW but not low MW dextran sulfate—such as that used in the examples disclosed herein—inhibited aggregation of human neutrophil cells (Rochon, et al. 1994). Also, dextran sulfate slightly inhibited aggregation of mouse cerebellar cells, but heparin and fucoidan sulfate had no effect (Fisher and Schachner, 1988). In cases where inhibition of cell aggregation was observed, the inhibition is not complete as the case with insect cells. More importantly, there is no data in the literature correlating inhibition of aggregation with increase in recombinant protein yield. Inducing single cells into suspension with polyanions to increase protein yield is not known in the art.

An important consideration for some of the sulfated polyanions is cost. For example, dextran sulfate costs only 3 cents/L of medium compared to $26/L for heparin. Since a lot of the research labs using insect cells to make recombinant proteins have shifted to Tn5B1-4 cells, there is a market for media that can be used to rapidly obtain and maintain stable single-cell suspension of T. ni cells.

SUMMARY OF THE INVENTION

The present invention teaches using sulfated polyanions to rapidly induce and maintain single-cell suspension of TN5B1-4 cells which resulted in significant enhancement of recombinant protein production. A sulfated polyanion is added to the medium of an anchorage-dependent cell line. The cells which are in suspension after the addition of the sulfated polyanion are subcultured to a fresh culture medium including the sulfated polyanion.

This method has been shown to work with cell lines derived from the Cabbage Looper, *Trichoplusia ni*. Specifically, the normally anchorage-dependent cell line BTI-Tn-5B1-4, ATCC CRL 10859, was successfully induced to suspension conditions in serum free medium.

Some general features of an effective polymer for inducing single-cell formation have been identified. The polymer has to be sulfated: the higher the degree of sulfation, the better. Unsulfated polyanions, polycations, neutral polymers, disaccharides, and monosaccharides were not effective in inducing single-cell formation. A sugar backbone was not essential since a hydrocarbon backbone was equally effective.

The three most effective polyanions for single-cell formation were dextran sulfate, polyvinyl sulfate, and pentosan sulfate - all highly sulfated. Dextran sulfate is the least expensive ($1.3/g) and increases medium costs by only 3 cents/L at 25 µg/ml - not a significant cost upcharge with a medium that costs $5–30/L. Dextran sulfate works at a concentration of 25 µg/ml. The cost of dextran sulfate treatment is low compared to heparin which required a 20-fold higher level to induce single-cell suspension and would add $26/L to medium costs. More importantly, dextran sulfate does not block viral infection at multiplicity of infection (MOI) greater than 1 plaque forming unit (PFU) per cell whereas heparin is known to seriously inhibit infection, an attribute shared by polyvinyl sulfate.

The present invention also teaches a method of culturing a cell line induced to single cell suspension by a sulfated polyanion that significantly inhibits infection by a baculovirus. The cells are subcultured to a fresh culture medium without the sulfated polyanion, or the sulfated polyanion is neutralized with a polycation, then the cells are inoculated with the baculovirus. Once the cells are infected with the baculovirus, the sulfate polyanion is added back to the fresh culture medium.

The intrinsic advantage of TN5B1-4 cells over the commonly used SF cell lines in per cell production can now be realized using single-cell suspension of TN5B1-4 cells which eliminates the problems that have so far limited the use of *T. ni* cells for large-scale production, including difficulty of growing *T. ni* cells in suspension, the poor yield in suspension, and the inefficiency of scaling-up attached cultures. The optimum volumetric yield of SEAP in TN5B1-4 DS 5000 cells under elevated oxygen but unsupplemented medium is 6 to 11-fold higher than attached cultures, and 3-fold higher than the best yield obtained for SF21 cells in suspension at elevated oxygen and with nutrient supplementation. The optimal per cell production of β-galactosidase in TN5B1-4 cells was 350 U/ $10^6$ cells in unsupplemented medium compared to 140 U/ $10^6$ cells for SF21 cells with nutrient supplementation. The peak volumetric β-galactosidase yield of TN5B1-4 cells at $2 \times 10^6$ cells/ml in unsupplemented medium is lower compared to SF21 cells at $7 \times 10^6$ cells/ml in supplemented medium (705 vs. 855 U/ml) probably because of nutrient limitations in TN5B1-4 cells as indicated by the rapid decline in per cell production with increasing density. By maintaining specific productivity with appropriate nutrient supplementation, TN5B1-4 cells should easily surpass the peak volumetric yield of β-galactosidase in SF21 cells.

The intrinsic advantage in per cell production of TN5B 1-4 over the commonly used SF cell lines can now be realized in suspension culture by using inexpensive sulfated polyanions to rapidly induce and maintain single-cell suspension of TN5B1-4 cells which substantially enhanced protein production. High yields of up to 110 mg/L of the glycosylated, secreted protein human alkaline phosphatase and 2.3 g/L of the cytoplasmic protein β-galactosidase have been obtained under elevated oxygen. Nutrient supplementation might potentially increase these yields further.

DETAILED DESCRIPTION

This description teaches the methods, materials and results of tests to determine whether various compounds sharing a structural feature(s) of heparin (polymer, sugar backbone, negative charge, sulfate groups, carboxylate groups, disaccharides, monosaccharides) are effective agents for inducing single cell cultures of TN5B1-4 and if these cultures are more productive than cultures that contain clumps.

The present invention teaches that sulfated polyanions rapidly induce single-cell formation, which results in significantly enhanced protein production. Unsulfated polyanions, neutral polymers, polycations, disaccharides, and monosaccharides were not effective in inducing single cell populations. A sugar backbone was not essential for single-cell formation since a hydrocarbon backbone worked equally well. More importantly, two of the most effective polyanions, dextran sulfate and pentosan sulfate, do not significantly affect viral infection in contrast to heparin.

Polymers and reagents

Heparin, dextran sulfate, fucoidan sulfate, pentosan sulfate, sodium carboxymethylcellulose, hyaluronate, chondroitin sulfate, dermatan sulfate, heparin disaccharides, chondroitin disaccharides, dextran, polyvinyl sulfate, l-carrageenan, k-carregeenan, sodium polyphosphoric acid, polyphosphate, glucose 6-phosphate, fructose 6-phosphate, protamine sulfate, DEAE-dextran (from dextran of MW 500,000), Pluronic F68, Antifoam C, heparinase I, heparinase II, chondroitinase ABC, hyaluronidase, 4' 6-Diamino-2-phenylindole (DAPI), fluorescein isothiocynate-dextran (FITC-dextran, MW 40,000), 5-bromo-4-chloro-3-indolyl b-D-galactopyranoside (X-gal), and 5-bromo-4-chloro-3-indolyl phosphate (BCIP), and rhodamine B isothiocyanate (RITC-dextran, MW 40,000) were obtained from Sigma Chemicals (St. Louis, Mo.). Dextran sulfate used for colloidal titration (MW 50000, 19% sulfur) was obtained from ICN (Costa Mesa, Calif.). Cat-Floc (polydiallyldimethyl ammonium chloride, MW 40,000) was a gift from Calgon Co. (Pittsburgh, Pa.). FITC-dextran sulfate (MW 40,000) was purchased from Molecular Probes (Junction City, Oreg.). DNase I, lipase, and Proteinase-K were from Boehringer Mannhelm (Indianapolis, Ind.). [Methyl-$^3$H] thymidine was obtained from Amersham Life Science (Arlington Heights, Ill.).

Cell Lines, Virus, Media, and Routine Maintenance

Spodoptera frugiperda (IPLB-SF21-AE) and Trichoplusia ni BTI-TN5B1-4 cell lines were obtained from Dr. R. R. Granados at the Boyce Thompson Institute for Plant Research (Ithaca, N.Y.). TN5B1-4 is a novel cell line established from T. ni eggs, and is the source of the "High Five" cell line from Invitrogen, San Diego, Calif. A recombinant E2 strain of Autographa californica multiple nuclear polyhedrosis virus (AcMNPV) containing the E. coli lac Z gene fused to the polyhedrin gene (E2-b-Gal) was a gift from MicroGeneSys (Meriden, Conn.). A recombinant human alkaline phosphatase (SEAP) virus constructed using the BamHI cloning site of the pAcYM1 plasmid was obtained from Dr. H. A. Wood of Boyce Thompson Institute.

Suspension culture of TN5B1-4 cells was obtained from M. S. Donaldson (Cornell University). These cells were initiated from monolayer cells grown in TNM-FH medium (10% FBS) into spinner flasks at 160 rpm and adapted to the serum-free medium Ex-Cell 405 (JRH Biosciences, Lenexa, Kans.) by reducing the proportion of TNM-FH gradually until the cells were in Ex-Cell 405 after 4–6 passages. Cells formed clumps immediately when grown in suspension with over 50 percent of the cells in aggregates. The cells were subcultured without settling to avoid selecting for subclones. Hereafter, these cells are referred to as control cells.

Cell concentrations were determined using a Coulter Counter (Model ZM, Coulter Electronics, Hialeah, Fla.) and viability measured using the trypan-blue exclusion method. Control cells were dissociated using the procedure of Moreira et al., where the sample was passed 30 times through a 200 ml micropipette tip prior to counting. (Moreira, J. L., Alves, P. M., Aunins, J. G., Carrondo, M. J. T. 1994. Changes in animal cell natural aggregates in suspended batch cultures. Appl. Microbiol. Biotechnol. 41: 203–209.)

Unlabeled budded virus was produced during replication in SF21. Mid-exponential cells were harvested by centrifugation, resuspended in fresh medium at $2 \times 10^6$ cells/ml, and infected at a multiplicity of infection (MOI) of 2 plaque forming units per cell in spinner flasks. After 48 h at 28° C., the virus was harvested by centrifugation at 500×g for 10 minutes to remove cells and cell debris. The supernatant was further clarified by two consecutive centrifugation at 1000×g for 30 min. The resulting supernatant typically contained $1–2 \times 10^9$ plaque forming units (PFU)/ml.

Virus titer was determined using a modified end-point dilution method. Briefly, $1.5 \times 10^4$ SF21 cells in 50 ml were seeded into 96-well plates. 10 ml of diluted virus was added per well and the plates spun at 1000×g for 1 h. After 7 days at 28° C., 25 ml of 1 mg/ml X-gal or BCIP for 13-galactosidase and alkaline phosphatase virus, respectively, was added per well. The proportion of wells that turned blue was determined 4–6 h after substrate addition. In a typical assay, 4 plates of 24 wells/dilution per plate were used. The titer obtained from the modified end-point dilution assay is reproducible (±10%) and is at least two-fold higher than titers from conventional end-point dilution method without centrifugation and plaque assay because of optimized binding (manuscript in preparation). The MOI is defined as the number of plaque forming units added per cell where the number of plaque forming units was calculated from the modified end-point dilution titer.

Inducing single-cell with dextran sulfate

Heparin is a natural mucopolysaccharide composed of D-glucuronic acid and D-glucosamine, and is fairly nonhomogeneous with respect to molecular weight and degree of sulfation. To explore the importance of various structural features on single-cell formation, we first considered dextran sulfate—a synthetic analog of heparin obtained by esterification of dextran. Dextran sulfate has no carboxylate group, but is highly sulfated with a maximum substitution of 3 sulfate groups per glucose residue. The degree of sulfation in commercial preparations of dextran sulfate is 2–2.5 groups per sugar unit.

Dextran sulfate induced single-cell formation from clumped TN5B 1-4 suspension grown in Ex-Cell 405, a serum-free medium. Most of the clumps were dispersed within 2 days and eliminated in 4 days. More severe level of clumping was eliminated in two passages: the first passage at high dextran sulfate concentration and the second at a much lower level. After inducing single-cell formation, a concentration of 25 µg/ml of dextran sulfate 5000 was enough to maintain the single-cell population.

Three different molecular weights of dextran sulfate, derived from dextran of MW 5000, 20000, 500000, were evaluated. The toxicity increased with MW, with the 500000 MW being toxic at levels above 5 µg/ml. The efficacy of single-cell formation, however, increased inversely with MW, with the 5000 MW being most effective.

Adaptation from monolayer to suspension

Clump formation in serum-free medium can be arrested by adding dextran sulfate when adapting monolayer cells to suspension. Cells adapted without dextran sulfate formed clumps after a few passages; clumping became more severe with time but eventually leveled off at passage 10 where typical aggregate sizes of 30–100 cells were observed. In contrast, cells grown in the presence of 25 µg/ml dextran sulfate remained as single cells. Cells in dextran sulfate were readily adapted to suspension culture and exhibited better growth than control cells. Enhanced cell growth in dextran sulfate may be due to better nutrient and oxygen transport to single cells compared to clumped cells.

A stable single cell suspension of TN5B1-4 was obtained from the clumped suspension culture by the addition of 25 µg/ml of dextran sulfate (from dextran of MW 5,000; actual MW—12,500). The cells were passaged at least 5 times in medium containing dextran sulfate before use in experiments. Hereafter, these cells are referred to as DS 5000 cells.

TN5B1-4 suspension cells were grown in 50-ml spinner flasks (Bellco Glass, Vineland, N.J.) with a working volume of 40 ml at 160 rpm. SF21 cells were grown in similar vessels at 130 rpm in Ex-Cell 400 medium. The screw caps of the flasks were replaced with silicone foam closures for better oxygen transfer. Cells were passaged every 3 days.

Inducing single-cell formation in serum-containing media—from clumped suspension or directly from monolayer—was more difficult and higher levels of dextran sulfate, up to 300 µg/ml, were required. Although a substantial reduction in clumping was achieved, complete elimination of clumping was not possible. Serum may contain positively-charged proteins which can neutralize dextran sulfate.

Growth Kinetics

TN5B1-4 cells grown in spinner flasks with dextran sulfate had a doubling time of 20 h, and reached a maximum density of $5-6\times10^6$ cells/mi. Dextran sulfate 5000 does not affect the doubling time and the maximum cell density for levels between 25–600 mg/ml (dam not shown). The growth of TN5B1-4 DS 5000 cells in suspension was scaled-up to a 1.25 L Celligen reactor agitated with a marine impeller at 90 rpm. The cells were subcultured three times in this reactor with no clump formation. The doubling time was 20 h and a maximum density of $6-7\times10^6$ cells/ml was reached.

Inducing single-cell with various compounds

The ability to induce single-cell suspension was tested with other compounds. These tests not only identify other agents that may be useful, but also provide information on what features of dextran sulfate contribute to its effectiveness.

Compounds were evaluated for their ability to induce single cell suspension in 50-ml spinner flasks at 160 rpm. Control cells were passaged at least 10 times in suspension before they were used in any experiments. Control cells were seeded at $5\times10^5$ cells/ml, allowed to grow in the presence of the additive for 3 days, counted and observed in a microscope, and then subcultured at the same initial density. A qualitative score for reduction in clumping relative to control cells was assigned to cells grown in the presence of test compound at the end of the third passage. The protocol for enzyme treatment was the same, but the seeding density was $1\times10^6$ cells/ml and cells were evaluated after 24 h. This data is summarized in Table 1 below.

TABLE 1

Effect of Various Compounds on Inducing Single-cell Formation of TN5B1-4 Cells In Suspension Culture

| Polymer dissacharides | Conc. (μg/ml) | Clumpin[a] | MW (kd) | Sulfate/carboxylate per mono-saccharide | μeq/mg[c] | neq/ml | Virus Binding[f] |
|---|---|---|---|---|---|---|---|
| A. Polyanion | | | | | | | |
| dextran sulfate I | 15 | ++ | 12.5 | 2.4/0 | 5.9 | 89 | |
| dextran sulfate I | 25 | +++ | 12.5 | | | 148 | 42 ± 2 |
| dextran sulfate II | 25 | ++ | 100 | 2.4/0 | 5.9 | 148 | 82 ± 4 |
| Pentosan sulfate | 25 | + | 3 | 2/0 | 5.3 | 133 | 53 ± 3 |
| Pentosan sulfate | 100 | +++ | 3 | 2/0 | | 530 | 55 ± 9 |
| Heparin | 100 | ++ | 16–17 | 1–1.5/0.5 | 6.0 | 600 | 63 ± 3 |
| Heparin | 270 | ++ | 16–17 | | | 1,620 | |
| Heparin | 540 | +++ | 16–17 | | | 3,240 | |
| λ-carrageenan | 12.5 | – | 250–300 | 1–1.3/0 | 3.6 | 180 | |
| λ-carrageenan | 25[d] | ++ | 250–300 | | | 360 | 68 ± 3 |
| Fucoidan sulfate | 25 | + | 112 | 1/0 | 3.0 | 75 | 53 ± 1 |
| Fucoidan sulfate | 100 | ++ | 112 | | | 300 | 53 ± 1 |
| Chondroitin sulfate | 100 | + | 50 | 0.5/0.5 | 4.0 | 400 | 94 ± 3 |
| Chondroitin sulfate | 300 | ++ | 50 | | | 1,200 | |
| Dermatan sulfate | 100 | + | 24.9 | 0.5/0.5 | 4.0 | 400 | 65 ± 7 |
| Dermatan sulfate | 300 | ++ | 24.9 | | | 1,200 | |
| κ-carrageenan | 100 | – | 150–250 | 0.5/0 | 2.3 | 230 | 73 ± 6 |
| sodium CMC | 1000 | – | 90 | 0/1[b] | 4.2 | 4,200 | 107 ± 1 |
| Hyaluronate | 100 | – | 59–104 | 0/0.5 | 2.5 | 250 | 99 ± 1 |
| Polyphosphoric acid | 100 | – | 1–2 | [NaPO$_3$]$_n$ | 9.8 | 980 | 98 ± 1 |
| Polyphosphate | 100 | – | 1.4–2 | Na$_{15}$P$_{13}$O$_{40}$ – Na$_{20}$P$_{18}$O$_{55}$ | 9.5 | 950 | |
| Polyvinyl sulfate | 10 | ++ | >100 | [—CH—CH$_2$—] \| OSO$_3^-$K$^+$ | 6.2 | 62 | 52 ± 4 |
| | 25 | +++ | | | | 155 | 52 ± 1 |
| B. Polycation | | | | | | | |
| Protamine sulfate | 50 | – | 5 | | | | virus ppt. |
| DEAE dextran | 5[d] | – | 630 | | | | 74 ± 9 |
| C. Neutral polymer | | | | | | | |
| Dextran | 100 | – | 11.5 | | | | 97 ± 2 |
| Dextran | 100 | not tested | 580 | | | | 99 ± 3 |
| Pluronic F68 | 1000 | – | 84 | | | | 98 ± 2 |
| D. Disaccharides[e] | | | | | | | |
| Heparin | 100 | not tested | 0.6 | 1–1.5/0.5 | 6.0 | 600 | 103 ± 2 |
| Chondroitin sulfate | 100 | – | 0.5 | 0.5/0.5 | 4.0 | 400 | 99 ± 6 |

[a]+++ Single cells; ++ single cells plus few clumps of 10 cells maximum; + slight improvement over control; – no improvement.
[b]Estimated; maximum theoretical substitution is 3 but average commercial substitution is generally less than 1.5.
[c]Calculated from sulfur content if available or else from formula.
[d]Toxic above these levels.
[e]Enzymatic digests of the polysaccharides.
[f]For 30 min as a % of Control-Control refers to binding of virus to cells with no additive.

The efficacy of dextran sulfate in inducing single-cell formation suggests that carboxylate groups of heparin are not important. Indeed, polysaccharides with only carboxylate groups such as sodium carboxymethylcellulose and hyaluronate did not induce single-cell formation (Table 1). The carboxylates of these macromolecules are ionized at the pH of the medium. Table 1 lists a number of polysaccharides with various degrees of sulfation and carboxylation and their effect in inducing single-cell formation. Two different molecular weight dextran sulfates have been included to bracket potential variations in efficacy due to size. The efficacy of inducing single-cell formation increased with the degree of sulfation.

The charge of the polymer was not a sufficient condition for single-cell formation. Unsulfated polyanions such hyaluronate, polyphosphate, polyphosphoric acid, and carboxymethylcellulose did not induce single-cell formation. The sulfate group has some degree of specificity that cannot be attributed solely to its charge.

Neutral polymers such as dextran and Pluronic F68, and polycations such as protamine sulfate and DEAE-dextran were ineffective in dispersing clumped cells. The phosphorylated monosaccharides glucose 6-phosphate and fructose 6-phosphate were also ineffective.

The sugar backbone was not essential for single-cell formation. Polyvinyl sulfate, a highly sulfated polymer with a straight-chain hydrocarbon backbone, was as effective as dextran sulfate in dispersing clumped cells. Further, the polymeric form of the sulfated polyanion was essential for single-cell formation. Chondroitin disaccharides did not disperse clumped cells whereas the polymeric form was moderately effective.

The three most effective polyanions for single-cell formation were dextran sulfate, polyvinyl sulfate, and pentosan sulfate—all highly sulfated. For dextran sulfate and polyvinyl sulfate, 25 µg/ml was adequate to maintain single-cell suspension whereas 100 µg/ml of pentosan sulfate was necessary. At these concentrations, pentosan sulfate—and polyvinyl sulfate—treated cells grew with the same doubling time and reached the same maximum cell density as dextran sulfate cells and were grown up to 10 passages. TN5B1-4 has been maintained as single-cell suspension in spinner flasks for over 70 passages with 25 µg/ml of dextran sulfate 5000, without significantly affecting doubling time, maximum cell density, and protein production.

TN5B1-4 cells have been maintained in single-cell suspension with dextran sulfate in a variety of serum-free media, including Ex-Cell 400, Ex-Cell 405, Express-Five, and IPL 41-based media (personal communication, M. S. Donaldson). Inducing single-cell formation in serum-containing media was more difficult. Higher levels of dextran sulfate were required and although a substantial reduction in clumping was achieved, single-cell formation could not be induced. Serum may contain positively charged proteins which can neutralize dextran sulfate. The problem in serum-containing media is not a serious limitation since elimination of serum in suspension culture is desirable, because serum is expensive and comparable levels of recombinant proteins can be obtained in serum-free media.

Model for aggregation

The mechanism by which sulfated polyanions induce single-cell formation in insect cells is not entirely clear. Sulfated polysaccharides and phosphorylated monosaccharides have been shown to block the L-selectin-mediated aggregation of neutrophils. Such lectin-mediated adhesive interaction does not occur in TN5B 1-4 since phosphorylated monosaccharides did not inhibit aggregation, and a carbohydrate backbone was not essential for single-cell formation.

Other studies have shown that sulfated polysaccharides induce aggregation of mammalian cells, indicating that these compounds have no intrinsic capacity to disaggregate cultures, and, in fact, disaggregation is an unexpected result. Thurn and Underhill found that heparin and dextran sulfate induced aggregation in cells of lymphoid origins but not in cell lines of fibroblastic origins. The ability of heparin to induce aggregation is closely related to the binding affinity of heparin to the cell surface. Conditions such as a shift in pH or ionic strength which lower the binding affinity of heparin increase aggregation. Nakashima et al. reported that polyanions such as dextran sulfate induce aggregation of mouse lymphocytes.

There are three major types of non-specific interaction important for cell adhesion: electrostatic forces, steric stabilization, and van der Waals or electrodynamic forces. Bongrand and Bell estimated the van der Waals attraction to be smaller than the electrostatic and steric repulsive forces between two like cells and concluded that van der Waals attraction is not sufficient to cause cell-cell adhesion unless the electrostatic or steric repulsive forces are decreased. Indeed, when repulsive forces in TN5B1-4 cells were reduced by digesting the glycosaminoglycans, the cells aggregated more severely.

The surface of eucaryotic cells is surrounded by a carbohydrate-rich coat termed the glycocalyx. The glycocalyx is made up of short oligosaccharides bound to glycoproteins, glycolipids, and high-molecular-weight proteoglycans. The glycocalyx of mammalian cells is negatively charged because of the sulfation and carboxylation of the sugars in proteoglycans, and the presence of sialic acid residues. The glycocalyx of two approaching cells give rise to repulsive forces: electrostatic repulsion due to negative surface charges, and steric repulsive forces termed steric stabilization due to the presence of flexible polysaccharide molecules on the cell surface. These repulsive forces are important in preventing cell-cell adhesion. In TN5B1-4 cells, enzymatic digestion of glycosaminoglycans increased clumping significantly, from typical aggregate sizes of 30–100 cells to over 500 cells per clump. Glycosaminoglycans are the negatively-charged polysaccharide chains in proteoglycans which contribute substantially to electrostatic repulsion and steric stabilization.

The surface charge per area of TN5B1-4 and SF21 cells are of the same order of magnitude as endothelial cells whose surface is surrounded by a thick glycocalyx, and much greater than for human red blood cells where the charge arises from numerous sialic acid residues on the surface. The surface charge of TN5B1-4 and SF21 cells are two orders of magnitudes higher than the estimated contribution from the membrane bilayer, indicating the presence of a highly charged glycocalyx.

The surface charge per area of TN5B1-4 was twice that of SF21 cells, indicating higher levels of glycosaminoglycans and/or sialic acid residues. It is therefore reasonable to expect the repulsive forces in TN5B1-4 cells to be greater than SF21 cells. Since SF21 cells do not adhere to each other in suspension with their lower repulsive forces, clumping of TN5B1-4 cells probably involves specific bond formation from receptor-ligand interaction which can overcome the repulsive barrier. Treatment of cells with proteinase-K resulted in elimination of clumping, thereby implicating a protein in cell-cell adhesion. For protease-treated cells, FITC-dextran sulfate was still bound to membrane fragments, but these fragments were no longer associated with the cell surface.

A tentative model for the aggregation of TN5B1-4 cells and single-cell formation by sulfated polyanions is proposed. Adhesion receptors present on the surface of TN5B1-4, but not SF21 cells interact specifically with substrate on lysed membrane fragments causing aggregation of TN5B1-4 cells. Sulfated polyanions competitively bind to the substrate on the membrane fragments thus preventing aggregation of TN5B 1-4 cells. This model is consistent with: 1) the strong binding of dextran sulfate to membrane fragments in both TN5B1-4 and SF21 cells where the fragments were associated with aggregates or attached to single cells in TN5B1-4, but were not attached to SF21 cells, 2) the necessity for the sulfate group of dextran sulfate for binding to membrane fragments and single-cell formation, and 3) the induced single-cell formation in TN5B1-4 cells by proteinase-K which removed membrane fragments attached to cells presumably by removing the putative adhesion receptor.

Labeled virus

Recombinant E2-β-Gal budded virus labeled with [methyl-$^3$H]thymidine was prepared during replication in SF21 cells. Mid-exponential cells were harvested by centrifugation at 125×g for 5 min, resuspended at 6–7×10$^6$ cells/ml in fresh Ex-Cell 400, and infected at an MOI of 15–20. After 3 h, the cells were pelleted, resuspended in fresh medium at 2×10$^6$ cells/ml, and placed in 50-ml spinner flasks. Following incubation for 4 h, [methyl-$^3$H]thymidine (25 Ci/mmol) was added at 50 mCi/ml.

Labeled virus was harvested at day 2 and clarified as described for unlabeled virus. The virus was then pelleted at 13,000×g for 1 h and allowed to resuspend overnight in fresh medium. The virus was then repelleted, and resuspended overnight in fresh medium. Purified labeled virus had specific activities of 50,000–55,000 virus particles per DPM (disintegration per min). The number of particles was determined based on DNA content as described by Wickham et al. (1992). Over 99% of the radioactive counts was TCA-precipitable. However, only 91–93% of the virus was bound to TN5B1-4 after three consecutive 2 h incubations of the residual unbound virus with cells at high density. Because less than 2% of the radioactivity was solubilized by DNase, the remaining non-bindable activity is probably from naked viral nucleocapsids. The proportion of naked vital nucleocapsids is typical for purification of AcMNPV. Calculation of the particle/PFU ratio of purified virus from two separate preparations gave a range of 4–5 particles per PFU.

Binding inhibition

Sulfated polyanions are known to inhibit the binding of several viruses such as HIV-1 on lymphocyte cells and cytomegalovirus on human embryonic lung cultures (Baba et at., 1988; Neyts et al., 1992). Severe inhibition of baculovirus binding could be problematic because it can interfere with the infection process. In particular, synchronous infection may not possible, resulting in significant cell growth which competes for nutrients. Such competition could result in poor recombinant protein production.

Once the [$^3$H]thymidine-labeled budded virus was prepared, binding studies were carried out in suspension at 5×10$^6$ cells/ml in polymethacrylate cuvettes, stirred with a magnetic bar. Non-specific binding of virus to the cuvette was negligible. The attachment rate of the virus to single cells of TN5B1-4 DS 5000 which were washed twice and resuspended in fresh medium without dextran sulfate was equivalent to single cells obtained from control cells by settling the large clumps, and dissociating the remaining small aggregates by passing several times through a 5-ml pipette. Because of the tendency of control cells to re-aggregate, TN5B1-4 DS 5000 cells, washed twice and resuspended in fresh medium without dextran sulfate, were used as the source of single cells for binding studies.

Approximately 27,000–30,000 DPM (disintegration per min) of [$^3$H]-labeled virus (~300 virions/cell) was added to 1.4 ml of cell suspension or medium only containing the test compound, and incubated at 28° C. The cell-free control was included to determine if the test compound induced virus precipitation. After 30 min incubation, the samples were transferred to microcentrifuge tubes and spun at 250×g for 2 min. A 0.7 ml aliquot of the supernatant was dissolved in scintillation fluid (Ready-Solv HP, Beckman Instrument, Fullerton, Calif.), and counted in a Beckman LS6800 scintillation counter which automatically converted counts per min to DPM using a resident quench curve obtained with tritium quench standards (Beckmann Instrument). Counting efficiency was over 40 percent.

In general, polyanions that induced single-cell formation also inhibited virus binding (Table 1). For most of the sulfated polyanions, the amount of virus bound to cells in 30 min was 40–80% of the virus bound in the absence of polyanion, representing a two to six-fold decrease in the attachment rate constant assuming first order binding kinetics with respect to virus concentration.

The polymeric form was necessary for the binding inhibition since heparin, but not heparin disaccharides inhibited virus binding. Polycations at high concentration can induce virus precipitation such as the case with protamine sulfate. This precipitation is probably due to the bridging of the negatively-charged virus by the polycation, a phenomenon similar to the induced aggregation of charged liposomes by oppositely-charged polymers.

At concentrations required to maintain single-cell suspension of TN5B1-4, the three polyanions inhibited binding in the order dextran sulfate>pentosan sulfate=polyvinyl sulfate (Table 2). The binding of virus to TN5B 1-4 is very fast, with a rate constant that is about half of the maximum diffusion-limited binding. Dextran sulfate reduced the attachment rate constant six-fold, but binding was still significant, comparable to SF21 cultures without dextran sulfate. The binding of virus to TN5B1-4 in the presence of dextran sulfate and SF21 is reaction-limited.

TABLE 2

Effect of Sulfated Polyanions on AcMNPV Binding to TN5B1-4 Cells

| | Concentration (μg/ml) | Binding (% of control) |
|---|---|---|
| A. Binding in Presence of Polyanions[a] | | |
| Dextran Sulfate | 25 | 42 ± 2 |
| Polyvinyl Sulfate | 25 | 52 ± 4 |
| Pentosan Sulfate | 100 | 55 ± 9 |
| B. Pretreatment of Virus[b] | | |
| Dextran Sulfate | 25 | 103 ± 3 |
| Polyvinyl Sulfate | 25 | 96 ± 5 |
| Pentosan Sulfate | 100 | 99 ± 4 |
| C. Pretreatment of Cells[c] | | |
| Dextran Sulfate | 25 | 93 ± 9 |
| Polyvinyl Sulfate | 25 | 95 ± 6 |
| Pentosan Sulfate | 100 | 96 ± 7 |

[a]Binding at 5 × 10$^6$ cells/ml for 30 min; control is binding in absence of polyanion.
[b]Virus pretreated with polyanion for 2 h, pelleted at 13,000 × g for 1 h, resuspended in PBS, and allowed to bind to 5 × 10$^6$ cells/ml for 1 h without further polymer addition; control is untreated virus.
[c]Cells pretreated with polyanion for 3 h, washed once in Ex-Cell 405, and allowed to bind to 5 × 10$^6$ cells/ml for 1 h without further polymer addition; control is untreated cells.

Sulfated polyanions can reduce binding by interacting directly with the viruses. For example, dextran sulfate binds so strongly to Semliki Forest and influenza virus that the same level of binding inhibition is observed in the presence of dextran sulfate as with virus pretreated with the polyanion followed by extensive washing (Luscher-Mattli et al., 1992).

To establish if polyanions interact directly with the virus particle, labeled virus was pretreated with polyanions. The polyanions were then removed by a single wash with PBS buffer, and the virus samples used in binding assay. The results are summarized in Table 2. Pretreatment of the virus with polyanions did not affect binding, indicating that polyanions are not bound strongly to the virus. Similar pretreatment of cells with polyanions indicate that polyanions are also not bound strongly to the cells. Binding inhibition occurred only when polyanions were present during viral attachment.

The inhibition of binding was further explored by considering the effect of increasing polyanion concentration on the binding of virus to TN5B1-4 and SF21. Less than 20 μg/ml of both dextran sulfate and heparin were required to attain maximum inhibition. For heparin, no additional drop in binding was observed for up to 600 μg/ml. Dextran sulfate reduced the binding of the virus to TN5B1-4 but not to SF21. However, dextran sulfate inhibited viral infection in both cell lines, suggesting that inhibition of viral infection occurred at a step(s) subsequent to virus binding. The cell growth post-infection was used as a measure of virus infection since infection is known to inhibit cell division. Hereafter, synchronous infection is used to refer to infection with no measurable cell division post-infection.

The inhibitory effect of dextran sulfate on binding appears to be cell-specific, indicating that: 1) sulfated polyanions do not neutralize the virus directly, and 2) sulfated polyanions interact with cell surface components of TN5B1-4. It has been shown indirectly that sulfated polyanions do not bind strongly to TN5B1-4, however, the possibility of weak interactions which may be sufficient to inhibit binding still exists.

Binding was not completely inhibited in the presence of increasing levels of heparin and dextran sulfate. Instead, a maximum level of inhibition was reached, with no additional reduction in binding occurring beyond the threshold concentration. For heparin and dextran sulfate, the threshold value was less than 20 μg/ml. One possible explanation for this behavior is that the polyanion is bound to the cell surface, and reached saturation at the threshold value. Since the same amount of polyanion is bound at concentrations above the threshold value, no additional reduction in binding is observed. An example of such occurrence is the binding of heparin to the lymphoid cell line YAA-C1, where binding is weak with a $K_d$ of $3.5 \times 10^{-7}$ M, and the amount of bound heparin quickly reached saturation at 10 mg/ml (Thurn and Underhill, 1986). If sulfated polyanions reduce binding of baculovirus to TN5B1-4 by binding to the cell surface, the binding of the sulfated polyanions is very fast since the same binding inhibition was observed when the polyanions were added with the virus vs. incubation of cells with polyanions for extended period of time before virus addition.

Viral infection inhibition

At concentrations required to induce and maintain single-cell suspension of TN5B1-4, the three polyanions inhibited infection, but to varying degrees. The cells were infected at MOI of 0.1, 0.5, 1, 5, 10, and 20 to determine the lowest MOI for synchoronous infection.

For dextran sulfate and pentosan sulfate, viral infection was not severely inhibited for MOI≧1. In contrast, polyvinyl sulfate inhibited viral infection even at high MOI. The order of inhibition of viral infection was polyvinyl sulfate> >pentosan sulfate>dextran sulfate. This order is different from the order of binding inhibition, indicating that inhibition of infection was not due to the reduction in binding rate.

Additional evidence suggests binding is not the cause of reduced infectivity. First, dextran sulfate inhibited infection in SF21, but did not affect binding. Second, increased inhibition of viral infection in TN5B1-4 was observed by increasing the concentration of dextran sulfate above the threshold level where binding inhibition has already leveled off.

At concentrations required for single-cell formation, viral infection in TN5B1-4 was inhibited in the order: polyvinyl sulfate> >pentosan sulfate>dextran sulfate. Although these sulfated polyanions reduced virus binding to TN5B1-4, binding was still significant with the lowest binding rate still comparable to binding of virus to SF21, suggesting that inhibition of viral infection occurred at a step subsequent to binding. This hypothesis is confirmed with SF21 where dextran sulfate inhibited infection but not binding.

Different infection strategies are recommended for the various polyanions when using TN5B1-4 with the baculovirus expression vector system. For TN5B1-4 grown in dextran sulfate or pentosan sulfate, the cells can be synchronously infected in the presence of these polyanions at MOI≧1. For polyvinyl sulfate, which blocked infection severely, the polyanion can be removed transiently by resuspending the cells in polyanion-free media or by neutralizing with a polycation such as Cat-Floc before virus addition. An equivalent amount of polyvinyl sulfate is then added back after substantial amount of virus has been internalized. In general, a virus incubation time of 2 h at MOI≧2 before re-addition of polyvinyl sulfate should be adequate for synchronous infection at cell densities greater than $5 \times 10^5$ cells/ml. (Table 3)

Recombinant Protein Production

Cells were grown in 250-ml spinner flasks at 175 rpm to a density of $2.5-3.5 \times 10^6$ cells/ml, corresponding to mid-exponential phase. The cells were harvested by centrifugation at 125×g for 5 min, resuspended in fresh medium without dextran sulfate at $5-6 \times 10^6$ cells/ml for control cells and $8-10 \times 10^6$ cells/ml for DS 5000 cells. Virus was then added at a multiplicity of infection (MOI) of 20 plaque forming units per cell and allowed to attach for 2 h. Appropriate volumes of cells were then added to 50-ml spinner flasks, and made up to 40 ml with fresh medium to give the desired cell densities. Dextran sulfate was added back to DS 5000 cells at 25 μg/ml from a 10 mg/ml stock. Infection was allowed to proceed at 28° C. There was no measurable cell division post-infection for both control and DS 5000 cells. Both a cytoplasmic (β-gal) and a secreted (SEAP) recombinant protein were tested.

To compare recombinant protein production of cells passaged in different polyanions, cells were harvested by centrifugation at 125×g for 5 min, resuspended in fresh medium, and infected at $2 \times 10^6$ cells/ml with an MOI of 5 in the presence of the polyanion dextran sulfate and pentosan sulfate. Cells were grown for at least 5 passages in a particular polyanion before infection. Polyvinyl sulfate-treated cells were infected in the absence of polyvinyl sulfate which was added back 2 h after virus addition; this protocol was necessary to bypass the inhibition of viral infection by polyvinyl sulfate as discussed above.

Assay for β-Galactosidase Activity

Samples were removed, sonicated for 30 s to release intracellular b-galactosidase, and diluted in Z-buffer (0.06M $Na_2HPO_4$, 0.04M $NaH_2PO_4$, 0.01M KCl, 0.001M $MgSO_4$, and 0.05M b-mercaptoethanol, pH 7.6). β-galactosidase activity was measured based on the rate of cleavage of o-nitrophenyl β-D-galactoside (ONPG) at 28° C. Briefly, 10–25 ml of sample was added to 0.85 ml of Z-buffer. 100 ml of ONPG (100 mg/ml) was then added at time zero and incubated at 28° C. for 5–10 min, depending on the rate of color change. The reaction was stopped by adding 0.5 ml of 1M $Na_2CO_3$ and the $OD_{420}$ measured. The activity in International Units per milliliter was calculated using an extinction coefficient of 4.5 ml/mmol for o-nitrophenol:

IU/ml=(dilution factor)($OD_{420}$)(1450+ml sample)/(4.5 ml/mmol)(min of incubation) (ml sample) The values reported are the maximum values obtained 5–6 days pi. Yield can be converted to a milligram basis using a specific activity of 300 IU/mg for β-galactosidase.

Assay for SEAP activity

SEAP activity was measured based on the rate of hydrolysis of p-nitrophenyl phosphate (PNPP) to p-nitrophenol at 28° C. Briefly, 10 ml of sample was added to 1 ml of assay buffer (1.0M diethanolamine, pH 9.8, 0.5 mM $MgCl_2$ and 10 mM L-homoarginine) and 100 ml of PNPP (120 mM) and incubated at 28° C. The absorbance at 405 nm was monitored for 60 s, and the slope obtained. The activity in International Units per milliliter was calculated using an extinction coefficient of 18.8 ml/mmol for p-nitrophenol:

IU/ml=(dilution factor) (slope absorbance/min)(1110 ml)/ (10 ml)(18.8 ml/mmol) Samples for total SEAP activity were obtained by sonicating cells for 30 s and making appropriate dilutions in the assay buffer. For secreted activity, the cells were pelleted in a microcentrifuge for 10 s, and the supernatant assayed for SEAP activity. The values reported for total SEAP are the maximum values 4–5 days post-infection (pi). Yield can be converted to a milligram basis using a specific activity of 730 IU/mg for SEAP.

Figure 1A:
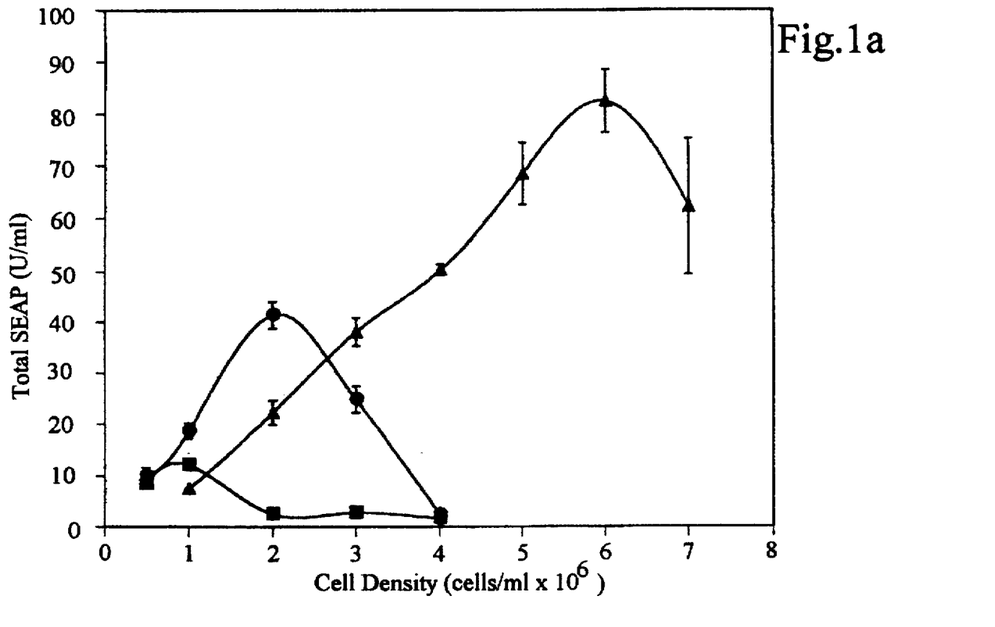
FIGS. 1a and 1b show volumetric yield and per cell production, respectively, for alkaline phosphatase expression for cells infected at MOI of 20 in 50-ml spinner flasks at 160 rpm in Ex-Cell 405. (■) Control TN5B1-4 cells at 21% gas-phase $O_2$; (●) TN5B1-4 DS 5000 cells at 21% gas-phase $O_2$; (▲) TN5B1-4 DS 5000 cells at 80% gas-phase $O_2$.
Figure 1B:
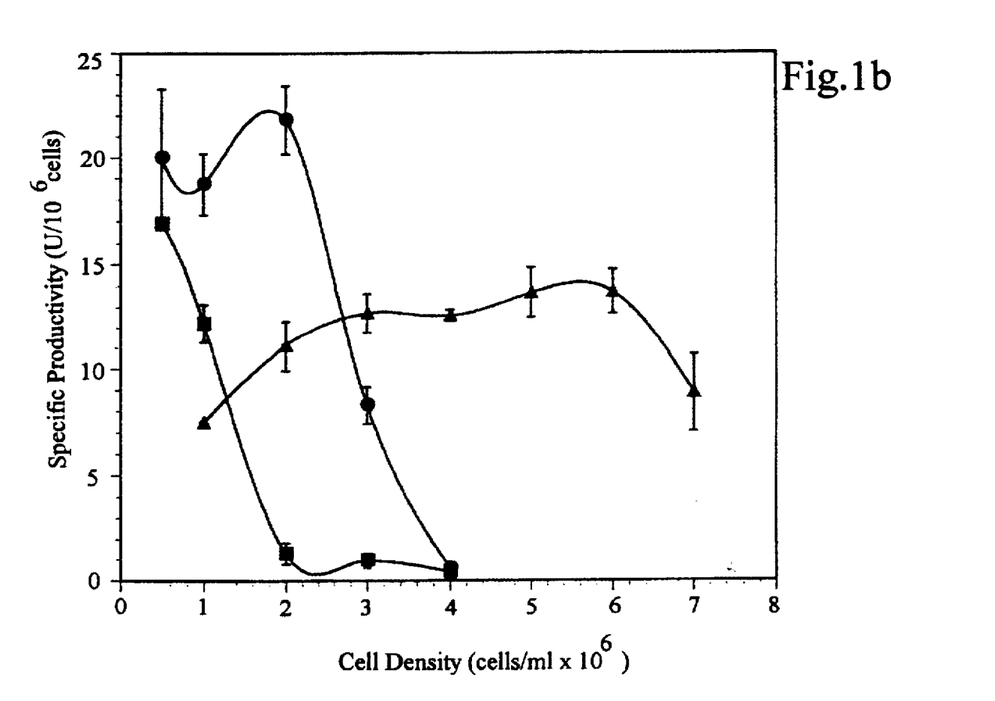

Dispersing clumped cells can potentially enhance protein production by eliminating cell-cell contact which has a deleterious effect on per cell production. FIGS. 1a and 1b show volumetric yield and per cell production, respectively, for alkaline phosphatase expression for cells infected at MOI of 20 in 50-ml spinner flasks at 160 rpm in Ex-Cell 405. (■) Control TN5B1-4 cells at 21% gas-phase $O_2$; (●) TN5B1-4 DS 5000 cells at 21% gas-phase $O_2$; (▲) TN5B1-4 DS 5000 cells at 80% gas-phase 02. Inducing single-cell formation with dextran sulfate resulted in a four-fold increase in volumetric yield of the recombinant glycosylated secreted protein alkaline phosphatase, and a two-fold increase in volumetric yield of the recombinant cytoplasmic protein β-galactosidase.

Figure 2A:
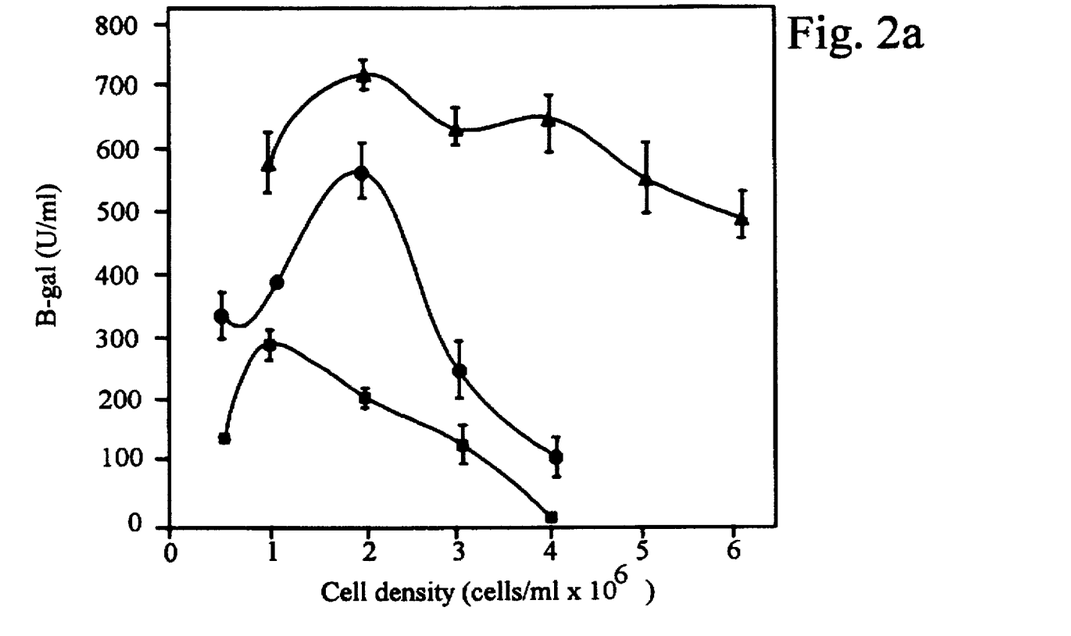
FIGS. 2a and 2b show volumetric yield and per cell production, respectively, for β-galactosidase expression for cells infected at MOI of 20 in 50-ml spinner flasks at 160 rpm in Ex-Cell 405. (■) Control TN5B1-4 cells at 21% gas-phase $O_2$; (●) TN5B1-4 DS 5000 cells at 21% gas-phase $O_2$; (▲) TN5B1-4 DS 5000 cells at 80% gas-phase $O_2$.
Figure 2B:
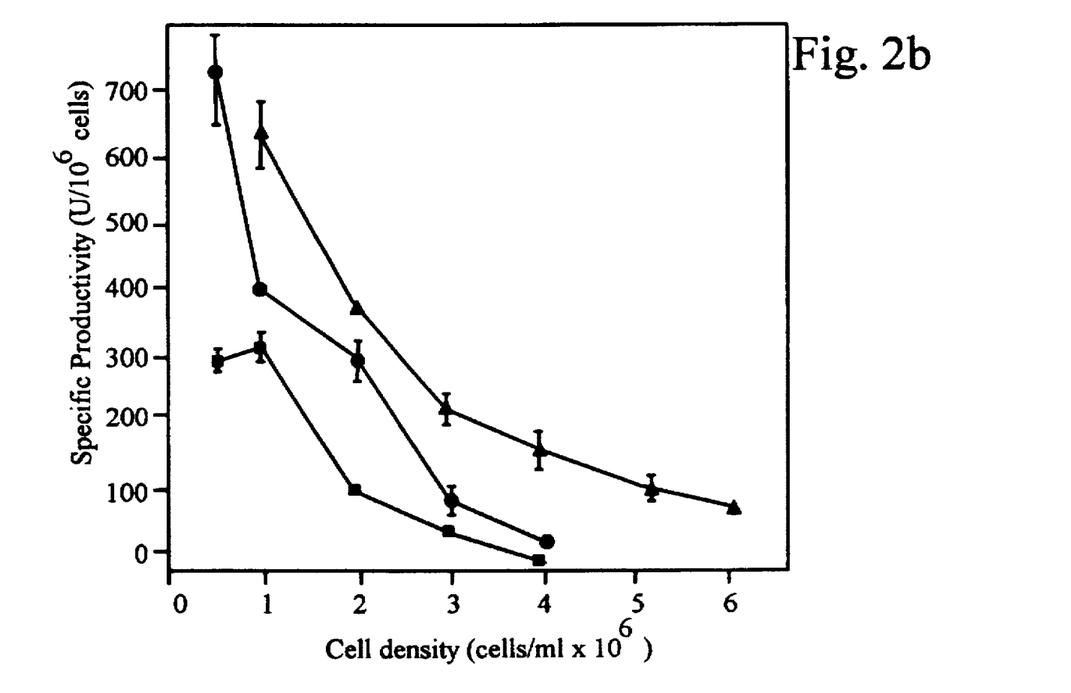

FIGS. 2a and 2b show volumetric yield and per cell production, respectively, for β-galactosidase expression for cells infected at MOI of 20 in 50-ml spinner flasks at 160 rpm in Ex-Cell 405. (■) Control TN5B1-4 cells at 21% gas-phase $O_2$; (●) TN5B1-4 DS 5000 cells at 21% gas-phase $O_2$; (▲) TN5B1-4 DS 5000 cells at 80% gas-phase $O_2$. For both proteins, increasing the gas phase oxygen concentration at high cell density enhanced protein production. High yields of 82 U/ml (110 mg/L) for alkaline phosphatase, and 705 U/ml (2.3 g/L) for β-galactosidase under elevated oxygen were obtained.

The per cell production of alkaline phosphatase in clumped suspension dropped drastically at cell densities over $1 \times 10^6$ cells/ml whereas per cell production in DS 5000 cells can be maintained over a wider range of densities especially with oxygen supplementation. In the case of β-galactosidase, per cell production even in DS 5000 cells dropped drastically with increasing cell density. The high level of β-galactosidase production indicates high levels of transcriptional/translational processes, which suggests a rate-limiting step(s) for alkaline phosphatase with respect to post-translational modifications and secretion.

The enhanced protein yield was not specific to dextran sulfate-treated cells since pentosan sulfate and polyvinyl sulfate treated cells produced as well (Table 3). The secretion level for alkaline phosphatase in the three polyanions was over 80 percent at day 3 when cell viability was still over 80 percent. Enhancement is probably just from single-cell formation since dextran sulfate did not enhance protein production in suspension of SF21 cells which are already single cells.

TABLE 3

Secreted Alkaline Phosphatase Expression using Different Infection Strategies (Ex-Cell 405, MOI = 5)*

| Polyanion (25 mg/ml) | Gas-Phase $O_2$ | Infection Strategy | % Secreted Day 3 | % Viability Day 3 | Total SEAP Day 5 (U/ml) |
|---|---|---|---|---|---|
| A. $2 \times 10^6$ cells/ml | | | | | |
| Clumped control | 21 | virus added directly to cells | — | >60 | 3 ± 2 |
| Dextran Sulfate (DS) | 21 | in presence of DS | 83 ± 2 | 83 ± 2 | 42 ± 4 |
| Pentosan Sulfate (PS) | 21 | in presence of PS | 90 ± 4 | 82 ± 2 | 41 ± 5 |
| Polyvinyl Sulfate (PVS) | 21 | strategy 1 | 87 ± 2 | 81 ± 1 | 45 ± 7 |
| Polyvinyl Sulfate | 21 | strategy 2 | 89 ± 4 | 83 ± 2 | 43 ± 5 |
| B. $5 \times 10^6$ cells/ml | | | | | |
| Clumped control | 80 | virus added directly to cells | — | — | 15⁺ |
| Dextran Sulfate | 80 | in presence of DS | 85 ± 3 | 72 ± 2 | 68 ± 4 |
| Polyvinyl Sulfate | 80 | strategy 2 | 89 ± 4 | 65 ± 3 | 64 ± 2 |

*Cells grown in polyanion for at least 5 passages before infecting in 50-ml spinner flasks. DS and PS cells were resuspended in fresh medium containing the polyanion before virus addition. Strategy 1: cells resuspended in polyanion-free medium, incubated with virus for 2 h before adding PVS back. Strategy 2: cells resuspended in PVS-containing medium, neutralized with Cat-Floc for 3 min, incubated with virus for 2 h before adding PVS back.
⁺From data of Taticek (1995)[23] at an MOI of 10

The present invention teaches using non-carboxylated sulfated polyanions to rapidly induce and maintain single-cell suspension of TN5B1-4 cells which resulted in significant enhancement of recombinant protein production. The enhancement may be a result of the elimination of cell—cell contact which is known to severely inhibit protein synthesis in attached cultures. Improved nutrient and oxygen transport to single cells versus clumped cells could also contribute to the increased yields. Also, single cells are more accessible to virus than clumped cells.

Some general features of an effective polymer for inducing single-cell formation have been identified. The polymer has to be sulfated: the higher the degree of sulfation, the better. Unsulfated polyanions, polycations, neutral polymers, disaccharides, and monosaccharides were not effective in inducing single-cell formation. A sugar backbone was not essential since a hydrocarbon backbone was equally effective.

The three most effective polyanions for single-cell formation were dextran sulfate, polyvinyl sulfate, and pentosan sulfate—all highly sulfated. Dextran sulfate is the least expensive ($1.3/g) and increases medium costs by only 3 cents/L at 25 mg/ml - not a significant cost upcharge with a medium that costs $5–30/L. The cost of dextran sulfate treatment is low compared to heparin which required a 20-fold higher level to induce single-cell suspension and would add $26/L to medium costs. More importantly, dextran sulfate does not block viral infection at $MOI \geq 1$ whereas heparin is known to seriously inhibit infection, an attribute shared by polyvinyl sulfate.

Non-carboxylated sulfated polyanions, i.e. dextran sulfate, pentosan sulfate, and polyvinyl sulfate, have been shown herein to work well. Those skilled in the art will be able to create new compounds that also work for the methods and media described herein. For example, sulfated polysaccharides, with a degree of sulfation per monosaccharide greater than 1.5, and sulfated hydrocarbon chains should work. Furthermore, derivatives of these compounds can be made that will work as well. For example, carboxymethyl dextran benzylamide sulfonate and a co-polymer of acryllic and polyvinyl sulfate are derivatives that will probably work at a slightly greater concentration than the compounds described above. Those skilled in the art can easily test the effectiveness of these derivatives using the techniques described herein The intrinsic advantage of TN5B1-4 cells over the commonly used SF cell lines in per cell production can now be realized using single-cell suspension of TN5B1-4 cells which eliminates the problems that have so far limited the use of T. ni cells for large-scale production, including difficulty of growing T. ni cells in suspension, the poor yield in suspension, and the inefficiency of scaling-up attached cultures. The optimum volumetric yield of SEAP in TN5B 1-4 DS 5000 cells under elevated oxygen but unsupplemented medium is 6 to 11-fold higher than attached cultures, and 3-fold higher than the best yield obtained for SF21 cells in suspension at elevated oxygen and with nutrient supplementation. The optimal per cell production of β-galactosidase in TN5B1-4 cells was 350 $U/10^6$ cells in unsupplemented medium compared to 140 $U/10^6$ cells for SF21 cells with nutrient supplementation. The peak volumetric β-galactosidase yield of TN5B1-4 cells at $2 \times 10^6$ cells/ml in unsupplemented medium is lower compared to SF21 cells at $7 \times 10^6$ cells/ml in supplemented medium (705 vs. 855 U/ml) probably because of nutrient limitations in TN5B1-4 cells as indicated by the rapid decline in per cell production with increasing density. By maintaining specific productivity with appropriate nutrient supplementation, TN5B1-4 cells should easily surpass the peak volumetric yield of β-galactosidase in SF21 cells.

The relative ease of post-translational modifications and secretion between cell lines can be compared by considering the weight ratio of a cytoplasmic protein to a glycosylated secreted protein. For example, the weight ratio of the cytoplasmic protein b-galactosidase to the glycosylated secreted protein SEAP for TN5B 1-4 was 40–50 compared to 80–100 obtained by Taticek (1995) for SF21 cells in suspension, indicating that post-translational modifications and secretion may be more severely limited in SF21 cells than in TN5B1-4 cells. A similar difference has been observed in attached cultures where the ratio is 60 for TN5B1-4 versus 160–200 for SF9 and SF21 cells. Although we have not considered virus production in this paper, M. S. Donaldson (personal communication) has shown that the virus titers obtained in TN5B1-4 DS 5000 cells are comparable to SF21 cells at $1-3 \times 10^9$ PFU/ml obtained by infecting at cell densities of $1-2 \times 10^6$ cells/ml.

The intrinsic advantage in per cell production of TN5B1-4 over the commonly used SF cell lines can now be realized in suspension culture by using inexpensive sulfated polyanions to rapidly induce and maintain single-cell suspension of TN5B1-4 cells which substantially enhanced protein production. High yields of up to 110 mg/L of the glycosylated, secreted protein human alkaline phosphatase and 2.3 g/L of the cytoplasmic protein β-galactosidase have been obtained under elevated oxygen. Nutrient supplementation might potentially increase these yields further.

Accordingly, it is to be understood that the embodiments of the invention herein described are merely illustrative of the application of the principles of the invention. Reference herein to details of the illustrated embodiments are not intended to limit the scope of the claims, which themselves recite those features regarded as essential to the invention.

What is claimed is:

1. A method of increasing single cell suspension in an insect cell line comprising the steps of:
   a) providing a culture of insect cells in a culture medium;
   b) adding an effective concentration of a non-carboxylated sulfated polyanion to said medium such that said cells are in suspension after the addition of said non-carboxylated sulfated polyanion; and
   c) subculturing said insect cells which are in suspension in a fresh culture medium including an effective concentration of said non-carboxylated sulfated polyanion.

2. The method of claim 1 in which said insect cell line is derived from a Cabbage Looper, Trichoplusia ni .

3. The method of claim 2 in which said insect cell line is BTI-Tn-5B1-4, ATCC CRL 10859.

4. The method of claim 1 in which said culture medium of step c) of claim 1 is serum free.

5. The method of claim 1 in which said non-carboxylated sulfated polyanion is selected from the group consisting of:
   i) dextran sulfate,
   ii) pentosan sulfate,
   iii) polyvinyl sulfate,
   iv) a sulfated hydrocarbon chain,
   v) a sulfated polysaccharide wherein the degree of sulfation per monosaccharide is greater than 1.5, and
   vi) derivatives of the compounds listed in subparagraphs i)–v).

6. The method of claim 1 in which said non-carboxylated sulfated polyanion is dextran sulfate added at a concentration of 25 µg/ml.

7. A culture of insect cells in a culture medium including a non-carboxylated sulfated polyanion, wherein said insect cells have been induced to single cell suspension by the method of claim 1, and wherein the non-carboxylated sulfated polyanion is present in an amount effective to carry out the method of claim 1.

8. A method of increasing single cell suspension in an insect cell line comprising the steps of:
a) providing a culture of insect cells in a culture medium;
b) adding an effective concentration of a sulfated polyanion to said medium such that said cells are in suspension after the addition of said sulfated polyanion, wherein said sulfated polyanion is selected from the group consisting of:
   i) dextran sulfate,
   ii) pentosan sulfate,
   iii) polyvinyl sulfate,
   iv) a sulfated hydrocarbon chain,
   v) a sulfated polysaccharide wherein the degree of sulfation per monosaccharide is greater than 1.5, and
   vi) derivatives of the compounds listed in subparagraphs i)–v); and
c) subculturing said insect cells which are in suspension in a fresh culture medium including an effective concentration of said non-carboxylated sulfated polyanion.

9. The method of claim 8 in which said insect cell line is derived from a Cabbage Looper, *Trichoplusia ni*.

10. The method of claim 9 in which said insect cell line is BTI-Tn-5B1-4, ATCC CRL 10859.

11. The method of claim 8 in which said culture medium of step c) of claim 8 is serum free.

12. A culture of insect cells in a culture medium including a non-carboxylated sulfated polyanion, wherein said insect cells have been induced to single cell suspension by the method of claim 8, and wherein the non-carboxylated sulfated polyanion is present in an amount effective to carry out the method of claim 8.

* * * * *